(12) United States Patent
Sadelain et al.

(10) Patent No.: US 8,058,061 B2
(45) Date of Patent: Nov. 15, 2011

(54) VECTOR ENCODING HUMAN GLOBIN GENE AND USE THEREOF IN TREATMENT OF HEMOGLOBINOPATHIES

(75) Inventors: Michel Sadelain, New York, NY (US); Stefano Rivella, New York, NY (US); Chad May, New York, NY (US); Joseph Bertino, Branford, CT (US)

(73) Assignee: Memorial Sloan-Kettering Cancer Center, New York City, NY (US)

( * ) Notice: Subject to any disclaimer, the term of this patent is extended or adjusted under 35 U.S.C. 154(b) by 147 days.

(21) Appl. No.: 12/433,412

(22) Filed: Apr. 30, 2009

(65) Prior Publication Data
US 2009/0274671 A1 Nov. 5, 2009

Related U.S. Application Data

(62) Division of application No. 10/188,221, filed on Jul. 1, 2002, now Pat. No. 7,541,179.

(60) Provisional application No. 60/301,861, filed on Jun. 29, 2001, provisional application No. 60/302,852, filed on Jul. 2, 2001.

(51) Int. Cl.
*C12N 5/00* (2006.01)
*C12N 15/00* (2006.01)
*C12N 15/67* (2006.01)
*C12N 15/11* (2006.01)

(52) U.S. Cl. ............. 435/325; 435/326; 435/320.1; 435/69.1; 536/24.1; 536/24.2

(58) Field of Classification Search ............... None
See application file for complete search history.

(56) References Cited

U.S. PATENT DOCUMENTS

| | | |
|---|---|---|
| 5,126,260 A | 6/1992 | Tuan et al. |
| 5,610,053 A | 3/1997 | Chung et al. |
| 5,631,162 A | 5/1997 | LeBoulch et al. |
| 5,834,256 A | 11/1998 | Finer et al. |
| 5,858,740 A | 1/1999 | Finer et al. |
| 5,981,276 A | 11/1999 | Sodroski et al. |
| 5,994,136 A | 11/1999 | Naldini et al. |
| 6,013,516 A | 1/2000 | Verma et al. |
| 6,090,608 A | 7/2000 | Oppenheim et al. |
| 6,110,666 A | 8/2000 | Grosveld et al. |
| 6,218,187 B1 | 4/2001 | Finer et al. |
| 6,294,165 B1 | 9/2001 | Lever et al. |
| 6,312,682 B1 | 11/2001 | Kingsman et al. |
| 6,428,953 B1 | 8/2002 | Naldini et al. |
| 6,444,421 B1 | 9/2002 | Chung |
| 6,524,851 B1 | 2/2003 | Ellis |
| 6,544,771 B1 | 4/2003 | Rivere et al. |
| 6,642,043 B1 | 11/2003 | Bertino et al. |
| 6,797,494 B1 | 9/2004 | Antoniou et al. |

FOREIGN PATENT DOCUMENTS
WO WO-97/33988 A1 9/1997

OTHER PUBLICATIONS

Walsh, C., et al., "Regulated High Level Expression of a Human Upsilon-Globin Gene Introduced into Erythroid Cells by an Adeno-Associated Virus Vector" Proceedings of the National Academy of Science (PNAS) 89(15): 7257-7261 (Aug. 1, 1992).
Collis et al, Definition of the minimal requirements within the human beta-globin gene and the dominant control region for high level expression, EMBO J, Jan. 1990; 9(1): 233-40.
D. Bodine, "Globin Gene Therapy: One (Seemingly) Small Vector Change, One Giant Leap in Optimism", Molecular Therapy, vol. 2, No. 2, pp. 101-102, Aug. 2000.
Dull et al. (1998) J. Virol. 72:8463-8471, "A Third-Generation Lentivirus Vector with a Conditional Packaging System".
Dzierzak et al., Lineage-specific expression of a human B-globin gene in murine bone marrow transplant recipients reconstituded with retrovirus-transduced stem cells., 1988, pp. 35-41, vol. 331.
Ercikan et al., "Effect of codon 22 mutations on substrate in inhibitor binding for human dihydrofolate reductase", Chemistry and Biology of Pteridines and Folates, pp. 515-519, 1993.
Gatlin et al. "In Vitro Selection of Lentivirus Vector-Transduced Human CD34+ Cells." Human Gene Therapy 11: 1949-1957 (2000).
Genbank NG-000007, priority date Jun. 19, 2006, downloaded Jul. 24, 2006.
Huang. et al., "Nonadditivity of Mutational Effects at the Folate Binding Site of *Escherichia coli* Dihydrofolate Reductase", Biochemistry, vol. 33, No. 38, pp. 11567-11585, 1994.
Kalberer et al., Preselection of retrovirally transduced bone marrow avoids subsequent stem cell gene silencing and age-dependent extinction of expression of human B-globin in engrafted mice, PNAS, 2000, pp. 5411-5415, vol. 97, No. 10.
May, et al., "Therapeutic haemoglobin synthesis in B-thalassaemic micc expressing lentivirus-encoded human b-globin", Nature, vol. 406, pp. 82-86, Jul. 6, 2000.
May et al., Successful treatment of murine B-thalassemia intermedia by transfer of the human B-globin gene, Blood 2002, pp. 1902-1908, vol. 99, No. 6.
Melton et al., Stability of HPRT marker gene expression at different gene-targeted loci: observing and overcoming a position effect, Nucleic Acids Research, 1997, vol. 25, No. 19 3937-3943.

(Continued)

*Primary Examiner* — Maria Marvich
(74) *Attorney, Agent, or Firm* — Edwards Angell Palmer & Dodge LLP; Peter C. Lauro, Esq.; Melissa Hunter-Ensor, Esq.

(57) ABSTRACT

Recombinant lentiviral vectors having a region encoding a functional β-globin gene; and large portions of the β-globin locus control regions which include DNase I hypersensitive sites HS2, HS3 and HS4 provides expression of β-globin when introduced into a mammal, for example a human, in vivo. Optionally, the vector further includes a region encoding a dihydrofolate reductase. The vector may be used in treatment of hemoglobinopathies, including β-thalessemia and sickle-cell disease. For example, hematopoietic progenitor or stem cells may be transformed ex vivo and then restored to the patient. Selection processes may be used to increase the percentage of transformed cells in the returned population. For example, a selection marker which makes transformed cells more drug resistant than untransformed cells allows selection by treatment of the cells with the corresponding drug.

15 Claims, 6 Drawing Sheets

OTHER PUBLICATIONS

Molete et al, Sequences flanking hypersensitive sites of the beta-globin locus control region are required for synergistic enhancement, MCB, May 2001; 21(9): 2969-80.

Naldini et al. (1996) Science 272:263-267, :In Vivo Gene Delivery and Stable Transduction of Nondividing Cells by a Lentiviral Vector. NG_000007 (GI:13907843), *Homo sapiens* genomic beta globin region on chomosome 11, U.S. National Library of Medicine, Bethesda, MD, USA, May 2001, accessed by PTO on Mar. 2, 2007.

Raftopoulos et al., Long-Term Transfer and Expression of the Human B-Globin Gene in a Mouse Transplant Model, Blood, 1997, pp. 3414-3422, vol. 90, No. 9.

Rivella et al., Genetic Treatment of Severe Hemoglobinopathies: The Combat Against Transgene Variegation and Transgene Silencing, Seminars in Hematology, 1998, pp. 112-125, vol. 35, No. 2.

Rivella et al. "Globin Gene Transter: a Paradigm for Transgenic Regulation and Vector Safety." Gene Therapy and Regulation 00:0; 1-27 (2003).

Ryan et al., A single erythroid-specific DNAse I super-hypersensitive site activates high levels of human b-globin gene expression in transgenic mice, Genes and Development, vol. 3, pp. 314-323, (see entire document), 1989.

Sabatino et al., Long-term expression of y-globin mRNA in mouse erythrocytes from retrovirus vectors containing the human y-globin gene . . . , PNAS, 2000, pp. 13294-13299, vol. 97, No. 24.

Sadelain et al. (1995) Proc. Natl. Acad. Sci. 92:6728-6732, "Generation of a high-titer retroviral vector capable of expressing high levels of the human B-globin gene".

Sadelain "Genetic Treatment of the Haemogloinopathies Recombinations and New Combinations." British Journal of Haematology 98: 247-253 (1997).

Sadelain et al. Issues in the Manufacture and Trsnplantation of Genetically Modified Hematopoietic Stem Cells. Current Opinion in Hematology 7: 364-377 (2000).

Sorrentino et al, Localization and characterization of the DNase I-hypersensitive site II (HS II) enhancer. A critical regulatory element within the beta-globin locus-activating region, Ann NY Acad Sci, 1990;612:141-51.

Tisdale et al. "Towards Gene Therapy for Disorders of Golbin Synthesis." Seminars in Hematology 38:4 382-392 (2001).

Zufferey et al., "Self-Inactivating Lentibirus Vector for Safe and Efficient in Vivo Gene Delivery", Journal of Virology, Dec. 1998, vol. 72, pp. 9873-9880.

VECTOR ENCODING HUMAN GLOBIN GENE AND USE THEREOF IN TREATMENT OF HEMOGLOBINOPATHIES

STATEMENT CONCERNING RELATED APPLICATIONS

This application is a divisional application of U.S. Ser. No. 10/188,221, filed Jul. 1, 2002, now U.S. Pat. No. 7,541,179, which claims the benefit of U.S. Provisional Application No. 60/301,861 filed Jun. 29, 2001 and U.S. Provisional Application No. 60/302,852 filed Jul. 2, 2001, each of which is incorporated herein by reference.

STATEMENT CONCERNING GOVERNMENT FUNDING

The invention disclosed in this application was made with funds provided under NHLBI grant No. HL57612. The United States government has certain rights in the invention.

BACKGROUND OF THE INVENTION

This application relates to a vector comprising a mammalian, and particularly a human globin gene and to the use thereof in treatment of hemoglobinopathies, including α- and β-thalessemia and sickle-cell disease.

Current treatment modalities for β-thalassemias consist of either red blood cell transfusion plus iron chelation (which extends survival but is cumbersome, expensive and an imperfect therapy), or allogeneic bone marrow transplant (which carries a lethal risk and is not available to the majority of patients). Thus, there is a substantial need for improved therapeutic approaches. The present invention provides a genetic correction in autologous hematopoietic stem cells, thus using gene therapy to provide a less-risky and more effective long-term treatment.

While gene therapy has been proposed for many years, a significant challenge facing efforts to develop gene therapy vectors is the ability to produce therapeutically useful levels of a desired protein or peptide. The present invention provides a vector which is capable of providing therapeutically meaningful levels of human globin for sustained periods of time. This ability arises from the ability to transmit large genomic regulatory sequences that control expression of the therapeutic gene.

SUMMARY OF THE INVENTION

In accordance with the invention, a recombinant lentiviral vector is provided comprising:
  (a) a region comprising a functional globin gene; and
  (b) large portions of the β-globin locus control regions which include large portions of DNase 1 hypersensitive sites HS2, HS3 and HS4. The regions may be the complete site or some lesser site which provides the same functionality as the specific sequences set forth below. This vector provides expression of (β-globin when introduced into a mammal, for example a human, in vivo. Optionally, the vector further comprises a region encoding a dihydrofolate reductase.

By incorporation of different globin genes, the vector of the invention may be used in treatment of hemoglobinopathies, including α- and β-thalessemia and sickle-cell disease. For example, hematopoietic progenitor or stem cells may be transformed ex vivo and then restored to the patient. Selection processes may be used to increase the percentage of transformed cells in the returned population. For example, a selection marker which makes transformed cells more drug resistant than un-transformed cells allows selection by treatment of the cells with the corresponding drug. Selection and/or enrichment may also be carried out in vivo, for example using methotrexate or similar antifolates to select for cells rendered resistant by the expression from the vector of a dihydrofolate reductase (DHFR).

DETAILED DESCRIPTION OF THE INVENTION

In a first aspect of the present invention, a recombinant lentirviral vector is provided comprising:
  (a) a region comprising a functional globin gene; and
  (b) large portions of the (β-globin locus control regions, which include DNase I hypersensitive sites HS2, HS3 and HS4.

As used in the specification and claims hereof, the term "recombinant lentiviral vector" refers to an artificially created polynucleotide vector assembled from a lentiviral-vector and a plurality of additional segments as a result of human intervention and manipulation.

The term "functional globin gene" refers to a nucleotide sequence the expression of which leads to a globin that does not produce a hemoglobinopathy phenotype, and which is effective to provide therapeutic benefits to an individual with a defective globin gene. The functional globin gene may encode a wild-type globin appropriate for a mammalian individual to be treated, or it may be a mutant form of globin, preferably one which provides for superior properties, for example superior oxygen transport properties. The functional globin gene includes both exons and introns, as well as globin promoters and splice doners/acceptors. Suitably, the globin gene may encode α-globin, β-globin, or γ-globin. β-globin promoters may be sued with each of the globin genes.

The recombinant vectors of the invention also include large portions of the locus control region (LCR) which include DNase I hypersensitive sites HS2, HS3 and HS4. In prior studies, smaller nucleotide fragments spanning the core portions of HS2, HS3 and HS4 have been utilized. Sadelain et al. *Proc. Nat'l Acad. Sci.* (*USA*) 92: 6728-6732 (1995); Lebouich et al., *EMBO J.* 13: 3065-3076 (1994). The term "large portions" refers to portions of the locus control region which encompass larger portions of the hypersensitive sites as opposed to previously tested fragments including only the core elements. The regions may be the complete site or some lesser site which provides the same functionality as the specific sequences set forth below. In preferred embodiments of the invention, the large portions of the locus control regions are assembled from multiple fragments, each spanning one of the DNase I hypersensitive sites. In addition, the locus control region has two introduced GATA-1 binding sites at the junction between HS3 and HS4. While not intending to be bound by any specific mechanism, it is believed that the incorporation of these transcription factor binding sites enhances the effectiveness of the vector.

Figure 1:
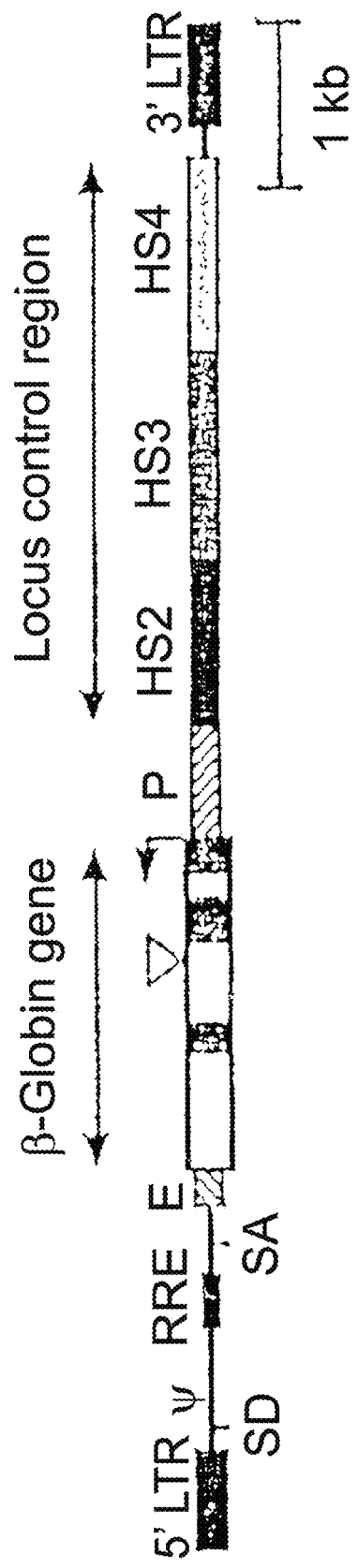
FIG. 1 shows the genomic structure of a recombinant oncoretroviral vector in accordance with the invention.

The genomic structure of one embodiment of the vector of the invention (TNS9) is shown in FIG. 1. TNS9 incorporates human β-globin gene (from position −618 to +2484) that includes an extended promoter sequence and a 3'-enhancer element. Optionally, a portion of 3' U3 region of the lentiviral backbone can be deleted for increased safety. In FIG. 1, the exons and introns of the human (β-globin gene are represented by filled and open boxes, The locations are indicated for the splice donor (SD), splice acceptor (SA), packaging region (ψ), rev-response element (RRE), human β-globin promoter (P) and 3'-β-globin enhancer (E). Thus, in the vector TNS9, a functional β-globin gene, which includes both the exons and introns of the gene and the relevant control sequences from the human β-globin locus. These are combined with the large fragments of the locus control region. The 3.2 kb LCR assembled into dTNS9 consists of an 840 bp HS2 fragment (SnaBI-BstXI), a 1308 by HS3 fragment (HindIII-BamHI) and a 1069 by HS4 fragment (BamHI-BanII).

In a further aspect of the invention, the (β-globin gene coding sequence can be exchanged and replaced with either the gamma globin gene (for sickle cell disease) or the alpha globin gene (for alpha-thalassemias). In one strategy, a NcoI-Pst I fragment of the (β-globin gene is replaced with the corresponding NcoI-HindIII fragment of the gamma globin gene or the NcoI-PstI fragment of the human alpha globin gene. These fragments start at the translational start of each globin gene (spanning the NcoI site) and end past their respective polyadenylation signals. In the second strategy, chimeric genes can be generated by only swapping the coding sequence of each one of the three exons of these genes. Thus, for the gamma globin gene, the result is a vector that comprises the beta globin promoter, the beta globin 5' untranslated region, the gamma exon 1 coding region, the gamma intron 1 the gamma exon 2, the beta intron 2, the gamma exon 3, and the beta 3' untranslated region. Thus all the elements of the TNS9 vector remain in place (promoter, enhancers, 5' and 3' untranslated regions, the LCR elements, the 2 additional GATA-1 binding sites and the introns of the beta globin gene (at least intron 2, which is most important). In a third strategy, the codon usage within exon 3 of the gamma globin gene can be modified so that its sequence will resemble as much as possible that of the beta globin gene. The reason for testing this is that the beta globin gene is always the best expressed.

Additional elements may be included in the vectors of the invention to facilitate utilization of the vector in therapy. For example, the vector may include selectable markers, to confirm the expression of the vector or to provide a basis for selection of transformed cells over untransformed cells, or control markers which allow targeted disruption of transformed cells, and thus the selective removal of such cells should termination of therapy become necessary.

In a further specific embodiment, the vector of the invention includes the mouse PGK promotor and human dihydrofolate reductase (DHFR) cDNA as a transcriptional unit. Mutant forms of DHFR which increase the capacity of the DHFR to confer resistance to drugs such as methotrexate are suitably used. For example, single and double mutants of DHFR with mutations at amino acids 22 and 31 as described in commonly assigned PCT Publication No. WO 97/33988, which is incorporated herein by reference, may be advantageously utilized.

Figure 2:
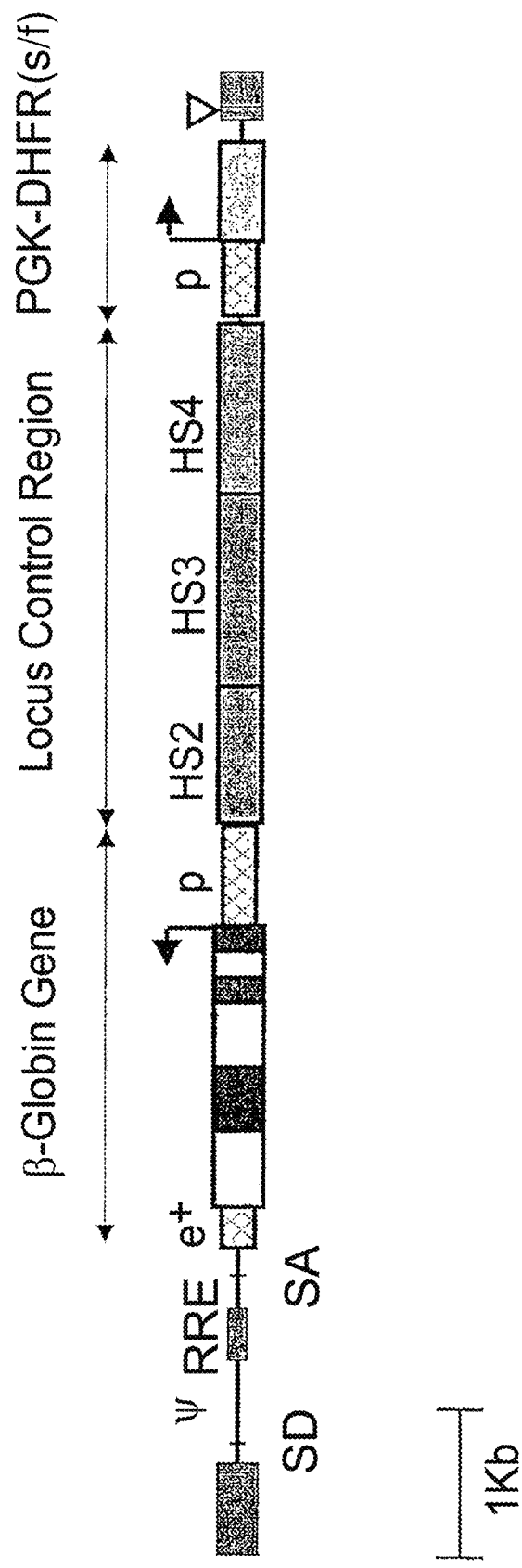
FIG. 2 shows the genomic structure of recombinant oncoretroviral vector within the scope of the invention.

FIG. 2 shows the genomic structure of specific vector within the scope of the invention. The vector includes a deleted LTR, from −456 to −9 of HIV LTR and the PGK promoter (530 bp) from the murine phosphoglycerate kinase 1 gene. It also includes a DHFR-encoding region encoding human DHFR with s/f mutation at amino acid 22. The locus control region and the β-globin region are the same as in TSN9. This vector is designated dTNS9-PD. This incorporation of DHFR into this vector provides transformed cells with a methotrexate-resistant phenotype. As a result, methotrexate, and other antifolates can be used, both in vitro and in vivo as a selection to tool to enhance levels of the functional hemoglobin. When hematopoietic stem cells were transformed using dTNS9-PD and reintroduced to mice that were then treated with NMBPR-P (0.5 mg/dose) and TMTX (0.5 mg dose) for five days, observed levels of expressed human β-globin were much higher in mice transduced with dTNS9-PD vectors after treatment with TMTX and NMBPR-P for selection of transduced cells.

The vectors of the invention are used in therapy for treatment of individuals suffering from hemoglobinopathies. In one embodiment of the invention, hematopoietic progenitor or stem cells are transformed ex vivo and then restored to the patient. As used in the specification and claims hereof, the term "hematopoietic progenitors and stem cells" encompasses hematopoietic cells and non-hematopoietic stem cells, e.g., embryonic stem cells, hematopoietic stem cell precursors, or any of the latter generated by nuclear transfer from a somatic cell. It is known in the art that efficient gene transfer into human embryonic stem cells can be achieved using lentiviral vectors.

Selection processes may be used to increase the percentage of transformed cells in the returned population. For example, a selection marker which makes transformed cells more drug resistant than un-transformed cells allows selection by treatment of the cells with the corresponding drug. When DHFR is used as a selection marker, it can be used for enrichment of transduced cells in vitro, or for in vivo selection to maintain the effectiveness of the vector.

The invention will now be further described with reference to the following non-limiting examples.

EXAMPLE 1

To produce vector TNS9, the human β-globin gene was subcloned from Mβ6L (Sadelain et al. *Proc. Nat I Acad. Sci. (USA)* 92: 6728-6732 (1995)) into lentiviral vector pHR'LacZ (Zuffery et al., Nature 15: 871-875 (1997)) replacing the CMV-LacZ sequence. pHR'eGFP was constructed by replacing LacZ with the eGFP sequence (Clontech). Viral stocks were generated by triple transfection of the recombinant vectors pCMVΔR8.9 (Zuffrey et al.) and pMD.G in 293T cells as previously described in Dull, et al., *J. Virol.* 72: 8463-8471 (1998). The pseudotyped virions were concentrated by ultracentrifugation resuspended and titrated as described in Gallardo et al., *Blood* 90: 952-957 (1997). For comparison, RSN1 was used which has a similar structure, except that the LCR contains only the core portion of HS2, HS3 and HS4. Northern blot analysis showed full length RNA transcripts, indicating that the recombinant lentiviral genomes are stable. Southern blot analysis on genomic DNA from transduced cells, digested once in each long terminal repeat (LTR) results in a single band corresponding to the expected size for the vector, indicating that the proviral structure is not rearranged.

EXAMPLE 2

To investigate the tissue specificity, stage specificity and expression level of the vector-encoded human B-globin gene, we transduced RNS1 and TNS9 into MEL cells, lymphoid Jurkat cells and myeloid HL-60 cells. Cell-free viral supernatant was used to infect C88 MEL cells in the presence of polybrene (8 µg ml$^{-1}$). Transduced MEL cells were subcloned by limiting dilution, and screened by PCR for transduction[36] using primers that anneal in the human β-globin promoter sequence (OPS, 5'-GTCTAAGTGATGACAGC-CGTACCTG-3'; SEQ ID NO:1) and in HS2 (C2A, 5'-TCAGCCTAGAGT GATGACTCC TATCTG-3'; SEQ ID NO:2). Vector copy number and integration site analysis was determined by Southern blot analysis[9]. Transduced MEL cells were induced to maturation by 5-day culture in 5 mM N,N'-hexamethylene bisacetamide (HMBA, Sigma).

Figure 3:
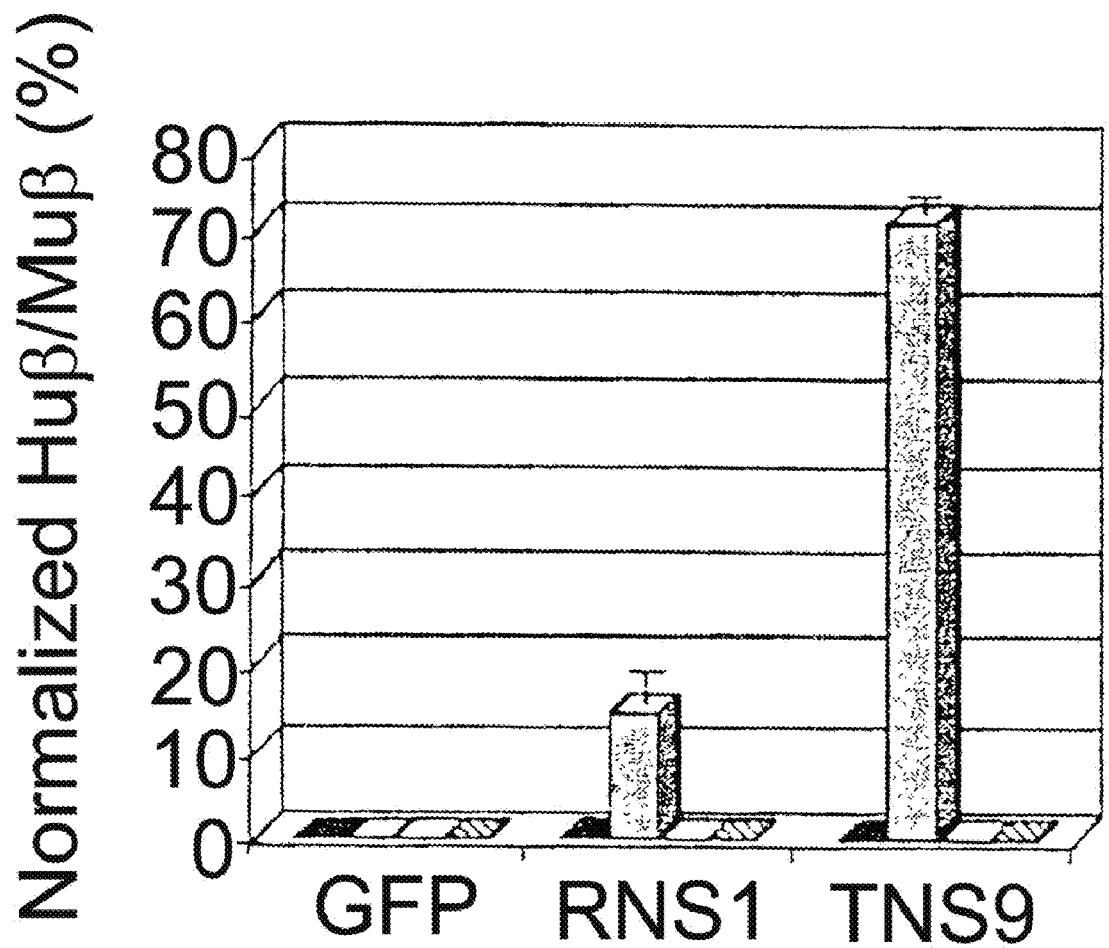
FIG. 3 shows experimental results demonstrating increased mean (β-globin expression in transduced MEL cells.

To induce (β-globin transcription, transduced MEL cell pools were differentiated using hexamethylene bisacetamide HMBA). Human (β-globin ($β^A$) and mouse (β-globin transcripts were measured by quantitative primer extension. After normalization to vector copy number and to endogenous β-globin expression per allele, human (β-globin levels were 14.2±4.7% for RNS1 and 71.3±2.3% for TNS9 in pooled MEL cells (FIG. 2a). MEL, Jurkat and HL-60 cells were transduced with RNS1, TNS9 or control GFP recombinant lentivirus. Human β-globin RNA expression in HMBA induced MEL cells (grey bars) was measured by quantitative primer extension and normalized to mouse β-globin RNA expression per locus. Expression was then normalized to the vector copy number determined by Southern blot. No human β-globin RNA expression was detected in non-induced MEL (black bars), Jurkat (white bars) or HL-60 cells (hatched bars), indicating that globin expression was erythroid- and differentiation-specific. No human β-globin expression was detected in non-induced MEL, Jurkat and HL-60 cells (FIG. 3), indicating that human β-globin expression was appropriately regulated in terms of tissue specificity and state of differentiation. We generated a panel of MEL cell clones that carried a single copy of either vector to distinguish whether the increased expression obtained in HMBA-treated Mel cells transduced with TNS9 rather than RNS1 was the result of an increase in $β^A$ expression per cell or of an increase in the fraction of cells expressing human β-globin. Transduced MEL cells were subcloned by limiting dilution immediately after transduction, avoiding any bias towards favourable chromosomal integration sites as produced by drug selection[5] The proportion of clones expressing human β-globin varied significantly between the two vectors. One out of ten RNS1 positive clones yielded measurable human β-globin transcripts, in contrast to 12 out of 12 for TNS9 also expressed higher levels of human β-globin than did those bearing RNS1 (P<0.01, Fisher's exact test). Cells bearing TNS9 also expressed higher levels of human β-globin than did those bearing RNS1 (P<0.01, Wilcoxon rank sum test). These findings established that both the level and probability of expression at random integration sites was increased with the TNS9 vector.

EXAMPLE 3

Quantification of Human β-Globin mRNA

Total RNA was extracted from MEL, Jurkat and HL-60 cells, or mouse spleen and blood using TRIzol. Quantitative primer extension assays were done using the Primer Extension System-AMV Reverse Transcriptase kit (Promega) with [$^{32}$p] dATP end-labelled primers specific for retroviral-derived human β-globin (5'-CAGTAACGGCAGACTTCTC-CTC-3'; SEQ ID NO:3) and mouse β-globin (5'-TGAT-GTCTGTTTCTGGGGTT GTG-3'; SEQ ID NO:4), with predicted extension products of 90 bp and 53 bp, respectively. The probes yield products of identical length for $β^{maj}$, $β^{min}$, $β^s$ and $β^1$. Primers were annealed to 4 µg of RNA and reactions were run according to manufacturer's protocols. Radioactive bands were quantitated by phosphorimager analysis (Bio-Rad). RNA isolated from A85.68 mice[20] was used as positive control. After correction for primer labelling, the human to mouse RNA signal was 29±1% per gene copy in repeated experiments (n>8), in agreement with previous findings based on RT-PCR[20]. Values measured in bone marrow chimaeras that were obtained in separate runs were standardized to the value obtained in the A85.68 RNA sample. In FIGS. 2 and 3c, d, human β-globin expression is expressed per vector copy and normalized to the endogenous transcripts (accounting for two endogenous alleles). In FIG. 3b, human transcripts are reported as the fraction of total β-globin RNA (Huβ/Huβ+Muβ) to reflect absolute contribution of vector-encoded transcripts.

EXAMPLE 4

To investigate the function of the vectors in vivo, we transduced and transplanted murine bone marrow cells without any selection in syngeneic, lethally irradiated recipient mice. Donor bone marrow was flushed from the femurs of 8- to 16-week-old male C57BL/6 or Hbb$^{th3/+mice}$ (Jackson Laboratories) that had been injected intravenously (i.v.) 6 days earlier with 5-flurouracil (5-FU, Pharmacia; 150 mg kg$^{-1}$ body weight). Bone marrow cells were resuspended in serum-free medium, and supplemented with IL-1α (10 ng ml$^{-1}$), IL-3 (100 U ml$^{-1}$), IL-6 (150 U ml$^{-1}$), Kit ligand (10 ng ml$^{-1}$ (Genzyme), β-mercaptoethanol (0.5 mM; Sigma), $_L$-glutamine (200 mM), penicillin (100 IU ml$^{-1}$) and streptomycin (100 µg m$^{-1}$), and cultured for 18 h. Recipient mice (11- to 14-week-old C57/BL6 or Hbb$^{th3/+}$ mice) were irradiated with 10.5 Gy (split dose 2×5.25 Gy) on the day of transplantation. Bone marrow cells were pelleted and resuspended in serum-free medium containing concentrated lentiviral supernatant, and supplemented with polybrene (8 µg ml$^{-1}$), $_L$-glutamine (200 mM), penicillin (100 IU ml$^{-1}$) and streptomycin (100 µg ml$^{-1}$), and cultured for 6 h. Transduced bone marrow cells (1×10$^5$ or 5×10$^5$) were then i.v. injected into each of the irradiated female recipients to establish short-term and long-term bone marrow chimaeras, respectively.

In short-term studies, spleens were removed 12 d after transplantation to extract total RNA and genomic DNA. To monitor long-term chimaeras, two or three capillary tubes of blood were collected every 4-6 weeks, from which genomic DNA, total RNA and haemoglobin were extracted. To examine vector function reliably in long-term animals, erythroid cell populations were purified from spleen. Single-cell suspensions were incubated with rat anti-mouse TER-119 monoclonal antibody (PharMingen). Sheep anti-Rat IgG dynabeads (M-450, Dynal Inc.) Were added to the antibody-coated spleen cells and purified as recommended by the manufacturer. Vector copy number, integration pattern and chimaerism were determined by Southern blot analysis. The fraction of donor DNA relative to recipient was determined by stripping and reprobing the blot with a [$^{32}$P] dCTP-labelled probe specific for the Y chromosome and normalizing to an endogenous mouse band. Radioactive bands were quantitated by phosphorimager analysis. Sera from five randomly selected long-term bone marrow chimaeras (30 weeks after transplantation) tested negative for HIV-1 gag by RT-PCR using the Amplicor HIV-1 monitor kit (Roche).

Figure 4:
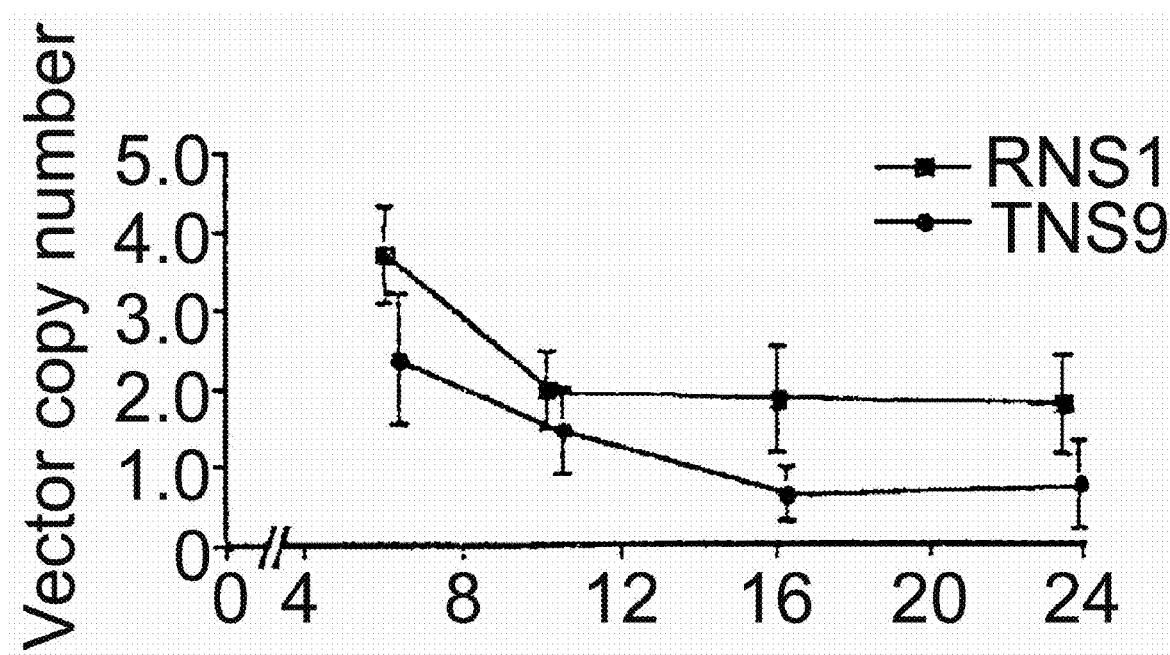
FIG. 4 shows the average vector copy number in peripheral blood cells, measured periodically for 24 weeks, which confirms highly efficient gene transfer in cells transduced with the vector of the invention.
Figure 5A:
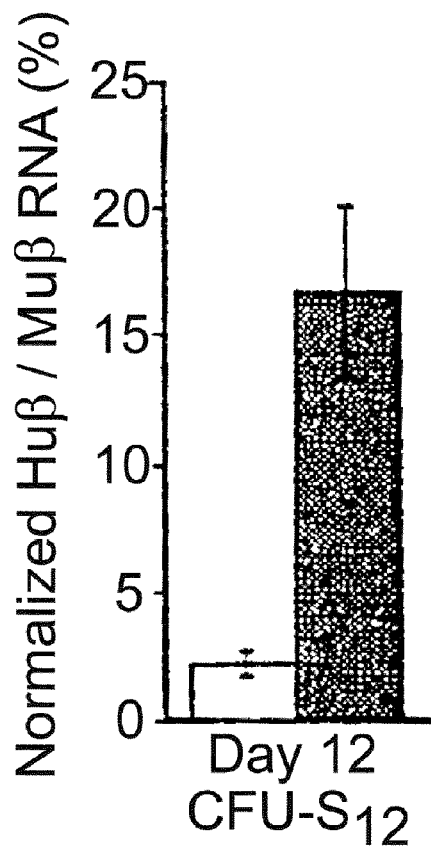
FIGS. 5A and B show human (β-globin expression per endogenous allele 12 days and 22 weeks after introduction of cells transduced with the vector of the invention.
Figure 5B:
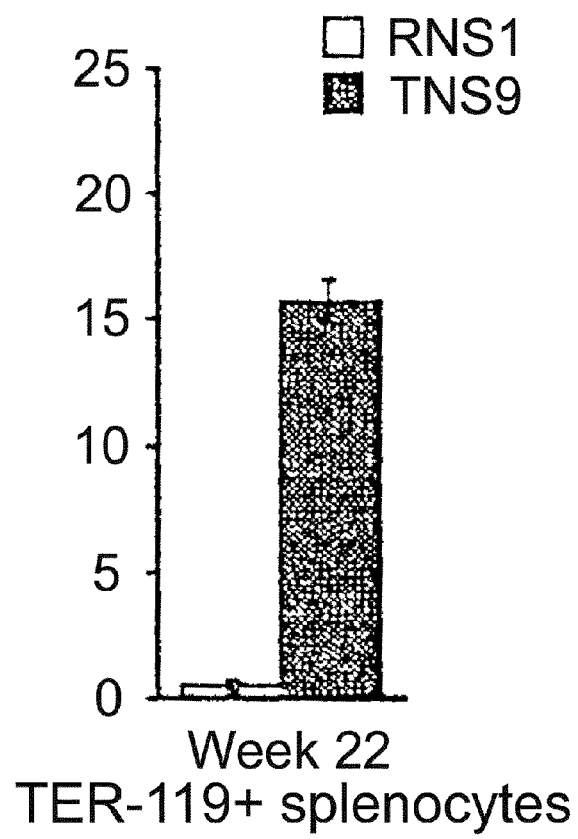

Vector copy number and human β-globin RNA transcripts were measured during a 24-week period in mice transplanted with RNS1 (n=8) or TNS9 (n=10) transduced bone marrow. a, Vector copy number was assessed by southern blot analysis of genomic DNA isolated from peripheral blood at weeks 6, 10, 16 and 24. The average vector copy number in peripheral blood cells, measured periodically for 24 weeks (FIG. 4), showed highly efficient gene transfer with both vectors (1.8±0.6 and 0.8±0.6 average vector copies per cell for β-globin transcript levels in the 10-20% range during the same time period. To assess transcriptional activity per vector copy, steady-state RNA transcripts and vector copy number were quantified in pooled $CFU-S_{12}$ and in erythroid TER-119+ spleen cells. Twelve days after transplantation, human β-globin expression per endogenous allele, (FIG. 5a). Twenty weeks later these values were 0.5±0.1% (significantly lower than on day 12, P=0.02) and 15.8±0.9% respectively (FIG. 5b). These findings established that the larger LCR fragments increased globin expression in vivo and, furthermore, suggested that TNS9 is more resistant to transcriptional silencing than is RNS1.

The levels of TNS9-encoded human β-globin could be produced. Haemoglobin tetramers incorporating vector-encoded human $β^A$ and endogenous murine c-globin (designated $Hbb^{hu}$) were quantitated in peripheral blood red cell lysates after cellulose acetate gel fractionation. $Hbb^{hu}$ levels accounting for up to 13% of total haemoglobin were found 24 weeks after transplantation (FIG. 3e, Table 1 in Supplementary Information). In the same assays, transgenic mice bearing one copy of a 230-kb yeast artificial chromosome (YAC) encompassing the entire human β-globin like gene cluster[20] showed 14% of their total haemoglobin incorporating human $β^A$. No haemoglobin tetramers containing human $β^A$ were measurable in any of the mice bearing RNS1 (table 1 in Supplementary Information). The proportion of mature peripheral blood red cells expressing human $β^A$ was elevate in most TNS9 bone marrow chimaeras, as shown by dual staining of human $β^A$ and TER-119. In contrast, chimaeras engrafted with RNS1-transduced bone marrow showed highly variable fractions of weakly staining $β^A$-positive erythrocytes. Normalized to the fraction of circulating $β^A$-positive mature red cells, the levels of haemoglobin containing lentivirus-encoded $β^A$ were on average 64% of those obtained in the YAC transgenic mice.

EXAMPLE 5

To ascertain that true HSCs were transduced, we carried out secondary transplants using marrow from primary recipients collected 24 weeks after transplantation. The TNS9 and RNS1 vectors were readily detected in all secondary recipients 13 weeks after transplantation. Human β-globin expression was maintained in all recipients of TNS9-transduced marrow. The successful transduction of HSCs was confirmed by integration site analyses. Southern blot analysis was performed on genomic DNA isolated from bone marrow, spleen and thymus of secondary bone marrow transplant recipients collected 13 weeks after transplant (one representative RNS1, and two representative TNS9 secondary transplant recipients are shown). Two endogenous bands are found in the genomic DNA of C57BL/6 (B6) mice.

EXAMPLE 6

Figure 6:
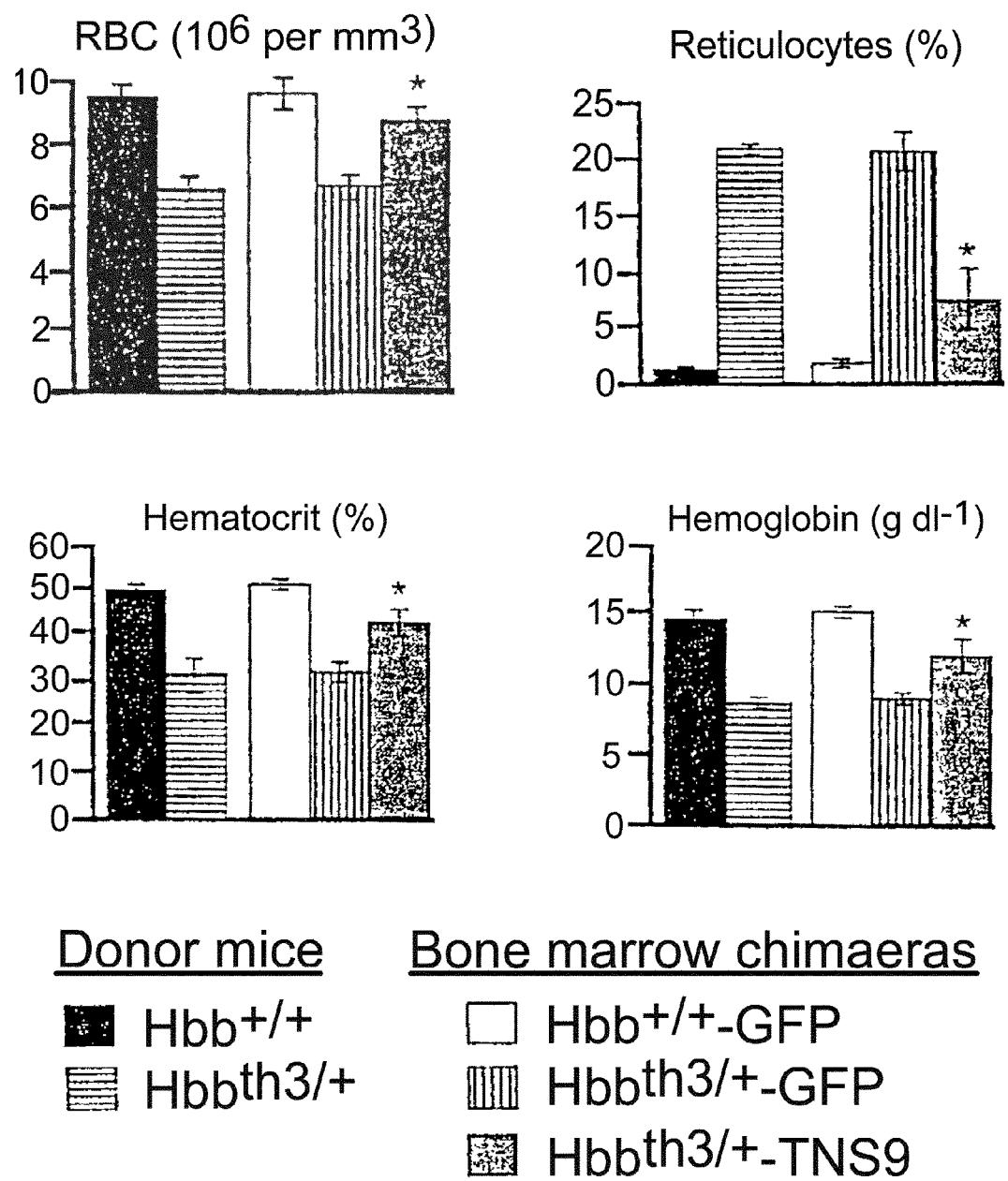
FIG. 6 shows haematocrit level, red blood cell count, reticulocyte count and haemoglobin level fifteen weeks after transplantation with unselected TNS9-transduced $Hbb^{th3/+}$ bone marrow.

In view of the high levels of expression, we tested the extent to which the TNS9 vector could correct the phenotype of thalassaemic cells using $β^0$-thalassaemic heterozygote mice that lack a copy of their b1 and b2 β-globin genes $(Hbb^{th3/+})^{21}$. These heterozygotes have a clinical phenotype similar to human thalassaemia intermedia and exhibit chronic anaemia (haematocrit 28-30%, haemoglobin 8-9 g dl$^{-1}$ and anomalies in red cell size (anisocytosis) and shape (poikilocytosis). Fifteen weeks after transplantation with unselected TNS9-transduced $Hbb^{th3/+}$ bone marrow, the haematocrit level, red blood cell count, reticulocyte count and haemoglobin level were markedly improved in five out of five recipient mice (FIG. 6). Anisocytosis and poikilocytosis were markedly reduced in the peripheral blood smears of chimaeras bearing the TNS9 vector. Control mice transplanted with $Hbb^{th3/+}$ bone marrow cells transduced with a vector encoding enhanced green fluorescent protein (eGFP) all remained severely anaemic (n=5, FIG. 6) and maintained their abnormal red cell morphology. These results establish that levels of circulating haemoglobin obtained with TNS9 were indeed therapeutically relevant.

The combined effect of the high efficiency of gene transfer and the absence of vector rearrangements afforded by the recombinant lentivirus carrying the β-globin gene and LCR configuration adopted in TNS9 yielded levels of human $β^A$ expression in the therapeutic range. The higher expression obtained with TNS9 compared with RNS1 was associated with a higher fraction of permissive integration sites in MEL cells and a higher fraction of human $β^A$-containing red blood cells in bone marrow chimaeras. RNS1, which carries a weaker enhancer, silenced over time whereas TNS9 retained undiminished transcriptional activity over the same time period and in secondary transplant recipients.

Higher levels of murine $α_2$: human $β^A{}_2$ tetramers were obtained in peripheral blood samples from recipients of TNS9-transduced $Hbb^{th3/+}$ bone marrow (21±3% of total haemoglobin, n=5, than with $Hbb^{+/+}$ bone marrow (6±4%, n+10). The two groups showed comparable peripheral blood vector copy numbers and levels of human β-globin RNA (0.8±0.2 compared with 0.8±0.6, and 16.8±6% compared with 10.8±7%, respectively). This observation is consistent with a competitive advantage of murine β-globin over human β-globin in associating with murine α-globin[22]. In thalassaemic patients, added human β-chain synthesis would improve the α:β chain imbalance and thus increase red cell survival and ameliorate the ineffective erythropiesis in these patients. In patients with sickle cell disease, transduced $β^A$ chains are expected to have an advantage over the $β^S$ chains produced by both endogenous genes in competing for the available α-chains[23]. Given that patients with S/β-thalassaemia whose HbA represents 10-30% of their total haemoglobin are very mildly affected[1,24], the clinical benefit of such an intervention would be highly significant.

EXAMPLE 7

To investigate long-term expression of the transduced human β-globin genes and its therapeutic efficacy, we generated bone marrow chimeras engrafted with TNS9-transduced $Hbb^{th3/+}$ bone marrow cells (n=5) and studied them over a 40-week period.

Donor bone marrow was flushed from the tumors of 8- to 16-week old male c57/BL6 or $Hbb^{th3/+}$ mice[23] obtain from Jackson Laboratories (Bar Harbor, Me.) that had been injected intravenously (IV) 6 days earlier with 5-flurouracil (5-FU) 150 mg/kg body weight obtained from Pharmacia (Piscataway, N.J.). Bone marrow cells were resuspended in X-VIVO-15 serum-free medium and supplemented with 10 ng/mL interleukin-1α (IL-1α), 100 U/mL IL-3, 150 U/mL IL-6, 10 ng/mL, Kit ligand obtained from Genzyme (Cambridge, Mass.), 0.5 mM β-mercaptoethanol obtained from Sigma (St. Louis, Mo.), 200-mM L-glutamine, 100 IU/mL penicillin, and 100 µg/mL streptomycin. Bone marrow cells were then pelleted and resuspended in serum-free medium containing concentrated lentiviral supernatant and supplemented with 8 mg/mL polybrene (Sigma), 200 mM $_L$-glutamine, 100 U/mL penicillin, 100 µg/mL streptomycin and cytokines as above, and cultured for 8 hours. Transduced bone marrow cells ($5 \times 10^5$) were then injected IV into each of the irradiated female recipients to establish bone marrow chimeras. Recipients mice (11- to 14-week-old C57/BL6 or Hbb$^{th3/+}$ mice) were irradiated with 10.5 Gy (Split dose 2×5.25 Gy) on the day of transplantation.

Age-matched chimeras engrafted with eGFP-transduced Hbb$^{th3/+-}$ (n=5) and Hbb$^{+/+}$ (n=5) bone marrow cells served as controls. Vector copy number was monitored in peripheral blood by quantitive Southern blot analysis, and found to remain stable, between 0.5 and 1.0 copy/cell on average (data not shown). Protein expression was assessed by quantitive hemoglobin analysis, to measure the proportion of hemoglobin tetramers that incorporate human $\beta^A$ (Hbb$^{hu}$, mu $\alpha_2$: hu$\beta^A_2$) or murine β-globin (Hbb$^{mu}$, mu$\alpha_2$:mu$\beta$2), and immunofluorescence, to determine the fraction of mature RBCs that contain human $\beta^A$ protein. Transgenic mice bearing one copy of a 230-kb yeast artificial chromosome encompassing the entire human β-globin-like gene cluster$_{28}$ served as reference, showing 14% of their total hemoglobin incorporating human $\beta^A$ and 100% $\beta^A$+RBCs[19,28] Hbb$^{hu}$ accounted for 19% to 22% of the total hemoglobin in TNS9 chimeras. These levels remained stable up to 40 weeks after transplantation. Over this same time period, the proportion of mature peripheral RBCs expressing human $\beta^A$ also remained elevated and stable (about 70% to 80%), as shown by dual staining of human $\beta^A$ and TER-119.

EXAMPLE 8

Long-Term Amelioration of Anemia

The stability of TNS9-encoded $\beta^A$ expression detected in peripheral blood suggested that long-term hematologic and systemic therapeutic benefits could be obtained. To investigate whether Hbb$^{hu}$ production would suffice to treat the anemia, we closely monitored hemoglobin parameters over 40 weeks. The marked increase in hemoglobin concentration, RBC counts, and hematocrit was sustained throughout this time period. Control mice that received transplants of eGFP-transduced Hbb$^{th3/+}$ bone marrow cells remained severely anemic, indicating that the transplantation procedure itself did not alter the anemic state. The reticulocyte counts decreased to 5% to 8% in TNS9 treated-chimeras, compared to 19% to 21% in control eGFP-treated Hbb$^{th3/+}$ chimeras and age-matched Hbb$^{th3/+}$ mice, suggesting an increase in RBC life span and a decrease in erythropoietic activity.

EXAMPLE 9

To determine the impact of sustained human β-globin gene expression on hematopoiesis, we studied the degree of splenomegaly (enlargement of the spleen) and EMH in 1-year-old chimeras and age-matched control mice. Spleen weights measured in Tns9-treated Hbb$^{th3/+}$ chimeras were indistinguishable from recipients of eGFP-transduced normal bone marrow, as were the total number of cells per spleen. In contrast, mice engrafted with eGFP-transduced Hbb$^{th3/+}$ bone marrow cells showed spleen weights and total cell numbers that were about 3-fold greater. The correction of spleen weight in TNS9 bone marrow chimeras corresponded to a concomitant normalization in total hematopoietic progenitor cell content. Spleen CFU-Es, BFUEs, and CFUs-GM were reduced to levels measured in recipients of eGFP-transduced Hbb$^{th+/+}$ bone marrow, whereas they remained elevated in control chimeras engrafted with eGFPtrasduced Hbb$^{th3/+}$ bone marrow cells and in age-matched Hbb$^{th3/+}$ mice, as previously observed in another murine model of β-thalassemias.[29]

The regression of EMH was corroborated by morphologic examination of spleen and liver in long-term chimeras and age-matched controls. Histopathology of spleens of mice that received transplants of eGFP-transduced Hbb$^{th3/+}$ marrow was virtually identical to that of spleen from control Hbb$^{th3/+}$ mice. Specifically, the red pulp was significantly expanded, accounting for 80% to 90% of the cross-sectional area, and densely occupied by nucleated erythroid precursors. The white pulp, based on cross-sectional area, was relatively decreased and the marginal zones were obscured by the large number of nucleated RBCs, reflecting major expansion of the red pulp and erythroid precursors. In TNS9-treated chimeras, the amount of red pulp was considerably decreased, accounting for only about 50% to 60% of the cross-sectional area. In addition, the number of nucleated erythroid precursors in the red pulp was decreased. Other immature hematopoietic cells were present in the red pulp, but much less frequently than in the spleens of control Hbb$^{th3/+-}$ thalassemic mice. The livers from TNS9-treated chimeras were similar to those of the normal control mice in that no EMH was detected. In contrast, livers from mice engrafted with eGFP transduced Hbb$^{th3/+}$ bone marrow cells showed several small foci of intrasinusoidal EMH.

EXAMPLE 10

Toxic iron accumulation in the organs of thalassemic patients is a consequence of RBC destruction and increased gastrointestinal iron uptake. To determine whether sustained expression from the TNS9 vector reduced iron overload, we studied tissue sections of liver and heart, stained using Gomori iron stain. No iron deposition was seen in the livers of normal Hbb$^{+/+}$ control mice, whereas Hbb$^{th3/+}$ mice showed variable amounts of iron, including some large aggregates. TNS9-transduced treated chimeras demonstrated low to undetectable levels of iron in the livers, whereas iron was readily detected in the livers of all mice that received transplants of eGFP-transduced Hbb$^{th3/+}$ bone marrow cells. No iron accumulation was found in the heart of treated or control mice, as previously observed in another murine model of β-thalassemia,[30] in contrast to what is found in the human disease.[1-3]

EXAMPLE 11

To assess to efficacy of in vivo selection for cells transduced with globin and DHFR-encoding vectors in accordance with the invention, using antifolates the following alternative protocols are used. In protocol 1, the recipient mice are treated daily for 5 days with MTX (25 mg/Kg) and NBMPR-P (20 mg/Kg), starting 6 weeks after administration of transduced bone marrow cells. In protocol 2, the recipient mice are treated daily for 5 days with TMTX (40 mg/Kg) and NBMPR-P (20 mg/Kg), starting 6 weeks after administration of transduced bone marrow cells. In protocol 3, the recipient mice, conditioned with busulphan rather than with gamma-irradiation, are treated daily for 5 days with TMTX (40 mg/Kg) and NBMPR-P (20 mg/Kg), starting 4 weeks after administration of transduced bone marrow cells. (TMTX (Neutrexin; US Bioscience); >MTX (Methotrexate LPF Sodium; Immunex); NBMPR-P (Nitrobenzylthioinosine 5'-monophpsphate disodium salt; Alberta nucleoside therapeutics). Protocol 3 is in principle the most attractive protocol as the recipients are not irradiated and furthermore not treated with a "myeloablative conditioning regimen". They are treated with a relatively milder conditioning regimen consisting of a "non-myeloablative" dose of busulphan. It is hoped that, in combination with "in vivo selection" mediated by DHFR/TMTX, the recipients could be satisfactorily engrafted without receiving a harsh pre-transplant treatment. This would be the way to go for treating subjects with severe hemoglobinopathies.

What is claimed is:

1. An isolated mammalian hematopoietic progenitor cell or an isolated mammalian stem cell comprising a recombinant lentiviral vector which comprises a nucleic acid encoding a functional globin operably linked to a 3.2-kb nucleotide fragment which consists essentially of three contiguous nucleotide fragments obtainable from a human β-globin locus control region (LCR), the three fragments being a BstXI and SnaBI, HS2-spanning nucleotide fragment of said LCR, a BamHI and HindIII, HS3-spanning nucleotide fragment of said LCR, and a BamHI and BanII, HS4-spanning nucleotide fragment of said LCR, said vector providing expression of the globin in a mammal in vivo.

2. The cell of claim 1, wherein the mammalian hematopoietic progenitor cell or the stem cell is a human cell.

3. The cell of claim 2, wherein said vector further comprises a nucleic acid encoding a selectable marker.

4. The cell of claim 3, wherein the selectable marker is a dihydrofolate reductase or a mutant dihydrofolate reductase having increased resistance to antifolates as compared to a wild-type dihydrofolate reductase.

5. The cell of claim 1, wherein said functional globin is a mutant globin.

6. The cell of claim 1, wherein said functional globin is a wild-type globin.

7. The cells of claim 1, wherein said functional globin is a β-globin.

8. The cell of claim 7, wherein said β-globin is a human β-globin.

9. The cell of claim 1, wherein said functional globin is a γ-globin.

10. The cell of claim 1, wherein said functional globin is an α-globin.

11. A method for making a mammalian hematopoietic progenitor cell or a mammalian stem cell composition which comprises
    (a) preparing a recombinant lentiviral vector comprising a nucleic acid encoding a functional globin operably linked to a 3.2-kb nucleotide fragment which consists essentially of three contiguous nucleotide fragments obtainable from a human β-globin locus control region (LCR), the three fragments being a BstXI and SnaBI, HS2-spanning nucleotide fragment of said LCR, a BamHI and HindIII, HS3-spanning nucleotide fragment of said LCR, and a BamHI and BanII, HS4-spanning nucleotide fragment of said LCR, said vector providing expression of the globin in a mammal in vivo; and (b) obtaining hematopoietic progenitor cells or stem cells from the mammalian individual, and transducing the cells with the recombinant vector.

12. The method of claim 11, wherein said vector further comprises a nucleic acid encoding a selectable marker.

13. The method of claim 12, wherein the selectable marker is a dihydrofolate reductase or a mutant dihydrofolate reductase having increased resistance to antifolates as compared to a wild-type dihydrofolate reductase.

14. The method of claim 13, which further comprises performing selection using an antifolate on the transduced cell.

15. The method of claim 11, wherein said functional globin is a human β-globin.

* * * * *

```
                        SEQUENCE LISTING

<160> NUMBER OF SEQ ID NOS: 4

<210> SEQ ID NO 1
<211> LENGTH: 25
<212> TYPE: DNA
<213> ORGANISM: human

<400> SEQUENCE: 1
gtctaagtga tgacagccgt acctg                                           25

<210> SEQ ID NO 2
<211> LENGTH: 27
<212> TYPE: DNA
<213> ORGANISM: human

<400> SEQUENCE: 2
tcagcctaga gtgatgactc ctatctg                                         27

<210> SEQ ID NO 3
<211> LENGTH: 22
<212> TYPE: DNA
<213> ORGANISM: human

<400> SEQUENCE: 3
cagtaacggc agacttctcc tc                                              22

<210> SEQ ID NO 4
<211> LENGTH: 23
<212> TYPE: DNA
<213> ORGANISM: mouse

<400> SEQUENCE: 4
tgatgtgtgt ttctggggtt gtg                                             23
```